(12) United States Patent
Kerr et al.

(10) Patent No.: US 10,675,046 B2
(45) Date of Patent: Jun. 9, 2020

(54) JAW, BLADE AND GAP MANUFACTURING FOR SURGICAL INSTRUMENTS WITH SMALL JAWS

(71) Applicant: COVIDIEN LP, Mansfield, MA (US)

(72) Inventors: Duane E. Kerr, Loveland, CO (US); David M. Garrison, Longmont, CO (US); Dylan R. Kingsley, Broomfield, CO (US); William H. Nau, Jr., Longmont, CO (US); Jeffrey R. Townsend, Longmont, CO (US); Jeffrey R. Unger, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 270 days.

(21) Appl. No.: 15/665,722

(22) Filed: Aug. 1, 2017

(65) Prior Publication Data
US 2017/0325831 A1 Nov. 16, 2017

Related U.S. Application Data

(62) Division of application No. 13/969,278, filed on Aug. 16, 2013, now Pat. No. 9,724,116, which is a division
(Continued)

(51) Int. Cl.
*A61B 17/285* (2006.01)
*A61B 17/295* (2006.01)
(Continued)

(52) U.S. Cl.
CPC .......... *A61B 17/285* (2013.01); *A61B 17/295* (2013.01); *A61B 18/1445* (2013.01);
(Continued)

(58) Field of Classification Search
CPC ................. A61B 17/295; A61B 17/285; A61B 2018/141; A61B 2018/1407
See application file for complete search history.

(56) References Cited

U.S. PATENT DOCUMENTS

| 3,786,814 A | 1/1974 | Armao |
| D249,549 S | 9/1978 | Pike |

(Continued)

FOREIGN PATENT DOCUMENTS

| CN | 201299462 Y | 9/2009 |
| DE | 2415263 A1 | 10/1975 |

(Continued)

OTHER PUBLICATIONS

Int'l Search Report EP 09 003813.4 dated Aug. 3, 2009.
(Continued)

*Primary Examiner* — Thomas McEvoy
(74) *Attorney, Agent, or Firm* — Carter, DeLuca & Farrell LLP

(57) ABSTRACT

An endoscopic forceps includes an elongate shaft defining an instrument axis. An end effector includes first and second jaw members each supporting an opposed sealing surface for clamping tissue. At least one of the jaw members is movable relative to the instrument axis such that the jaw members are movable between a first spaced-apart configuration and a second closed configuration for grasping tissue. A cutting instrument includes a reciprocating blade translatable relative to the sealing surfaces to sever tissue clamped between the jaw members. The reciprocating blade contacts an undersurface of at least one of the jaw members when the jaw members are in the second configuration to define a gap distance between the sealing surfaces. A handle adjacent the proximal end of the elongate shaft is operable to induce motion in the jaw members, and an actuator is operable to selectively translate the reciprocating blade.

5 Claims, 6 Drawing Sheets

Related U.S. Application Data of application No. 12/574,292, filed on Oct. 6, 2009, now Pat. No. 8,512,371.

(51) Int. Cl.
  *A61B 18/14* (2006.01)
  *A61B 17/3205* (2006.01)

(52) U.S. Cl.
  CPC ... *A61B 17/32056* (2013.01); *A61B 2018/141* (2013.01); *A61B 2018/1407* (2013.01); *A61B 2018/1412* (2013.01); *A61B 2018/1432* (2013.01); *A61B 2018/1455* (2013.01)

(56) References Cited

U.S. PATENT DOCUMENTS

| | | |
|---|---|---|
| D263,020 S | 2/1982 | Rau, III |
| 4,589,411 A | 5/1986 | Friedman |
| 4,608,981 A | 9/1986 | Rothfuss et al. |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| 5,307,976 A | 5/1994 | Olson et al. |
| 5,322,055 A | 6/1994 | Davison et al. |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| 5,665,100 A | 9/1997 | Yoon |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,726,694 B2 | 4/2004 | Blatter et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| 7,011,657 B2 | 3/2006 | Truckai et al. |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| 7,156,846 B2 | 1/2007 | Dycus et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,407,078 B2 | 8/2008 | Shelton, IV et al. |
| D582,038 S | 12/2008 | Swoyer et al. |
| 7,488,319 B2 | 2/2009 | Yates |
| 7,500,975 B2 | 3/2009 | Cunningham et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,758,577 B2 | 7/2010 | Nobis et al. |
| D621,503 S | 8/2010 | Otten et al. |
| 7,819,872 B2 | 10/2010 | Johnson et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 9,724,116 B2 | 8/2017 | Kerr et al. |
| 2003/0018331 A1* | 1/2003 | Dycus ............... A61B 18/1445 606/48 |
| 2003/0229344 A1 | 12/2003 | Dycus et al. |
| 2007/0213711 A1 | 9/2007 | Eder et al. |
| 2008/0009854 A1* | 1/2008 | Yates ..................... A61B 18/14 606/42 |
| 2008/0015575 A1 | 1/2008 | Odom et al. |
| 2011/0082456 A1* | 4/2011 | Welt ................... A61B 17/295 606/45 |
| 2013/0245623 A1 | 9/2013 | Twomey |
| 2013/0247343 A1 | 9/2013 | Horner et al. |
| 2013/0253489 A1 | 9/2013 | Nau, Jr. et al. |
| 2013/0255063 A1 | 10/2013 | Hart et al. |
| 2013/0267948 A1 | 10/2013 | Kerr et al. |
| 2013/0267949 A1 | 10/2013 | Kerr |
| 2013/0274736 A1 | 10/2013 | Garrison |
| 2013/0282010 A1 | 10/2013 | Mckenna et al. |
| 2013/0289561 A1 | 10/2013 | Waaler et al. |
| 2013/0296856 A1 | 11/2013 | Unger et al. |
| 2013/0296922 A1 | 11/2013 | Allen, IV et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 102004026179 A1 | 12/2005 |
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 102008018406 B3 | 7/2009 |
| EP | 1281878 A1 | 2/2003 |
| EP | 1159850 A3 | 3/2003 |
| EP | 1769766 A1 | 4/2007 |
| JP | 61501068 | 9/1984 |
| JP | 1024051 | 1/1989 |
| JP | 55106 | 1/1993 |
| JP | 540112 | 2/1993 |
| JP | 65502328 | 3/1994 |
| JP | 6121797 | 5/1994 |
| JP | 6285078 | 10/1994 |
| JP | 06343604 A | 12/1994 |
| JP | 6511401 | 12/1994 |
| JP | 07265328 A | 10/1995 |
| JP | 08056955 A | 3/1996 |
| JP | 08252263 A | 10/1996 |
| JP | 8289895 | 11/1996 |

(56) References Cited

FOREIGN PATENT DOCUMENTS

| | | |
|---|---|---|
| JP | 8317934 | 12/1996 |
| JP | 8317936 | 12/1996 |
| JP | 9000538 | 1/1997 |
| JP | 09010223 A | 1/1997 |
| JP | 9122138 | 5/1997 |
| JP | 10000195 | 1/1998 |
| JP | 10155798 | 6/1998 |
| JP | 1147149 | 2/1999 |
| JP | 1147150 | 2/1999 |
| JP | 11070124 | 3/1999 |
| JP | 11169381 | 6/1999 |
| JP | 11192238 | 7/1999 |
| JP | 11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 20018944 | 1/2001 |
| JP | 200129355 | 2/2001 |
| JP | 200129356 | 2/2001 |
| JP | 2001128990 A | 5/2001 |
| JP | 2001190564 A | 7/2001 |
| JP | 20013400 | 11/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2011125195 A | 6/2011 |
| JP | 6030945 B2 | 11/2016 |
| SU | 401367 A1 | 10/1973 |
| WO | 0036986 A1 | 6/2000 |
| WO | 0059392 A11 | 10/2000 |
| WO | 0115614 A1 | 3/2001 |
| WO | 0154604 A1 | 8/2001 |
| WO | 0245589 A2 | 6/2002 |
| WO | 2006021269 A1 | 3/2006 |
| WO | 05110264 A3 | 4/2006 |
| WO | 2008040483 A1 | 4/2008 |
| WO | 2011018154 A1 | 2/2011 |

OTHER PUBLICATIONS

Int'l Search Report EP 09 004491.8 dated Sep. 9, 2009.
Int'l Search Report EP 09 005575.7 dated Sep. 9, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCTTUS03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—E p 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.

(56) References Cited

OTHER PUBLICATIONS

Carbonell et al., "Comparison of theGyrus PlasmaKinectic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.

* cited by examiner

JAW, BLADE AND GAP MANUFACTURING FOR SURGICAL INSTRUMENTS WITH SMALL JAWS

CROSS-REFERENCE TO RELATED APPLICATIONS

This application is a divisional of U.S. patent application Ser. No. 13/969,278, filed Aug. 16, 2013, which is a divisional of U.S. patent application Ser. No. 12/574,292, filed Oct. 6, 2009, now U.S. Pat. No. 8,512,371. The entire contents of each of the above applications are hereby incorporated by reference.

BACKGROUND

1. Technical Field

The present disclosure relates generally to endoscopic surgical instruments, and in particular to component arrangements and manufacturing processes suitable for use with instruments having relatively small end effectors.

2. Background of Related Art

Typically in a laparoscopic, an endoscopic, or other minimally invasive surgical procedure, a small incision or puncture is made in a patient's body. A cannula is then inserted into a body cavity through the incision, which provides a passageway for inserting various surgical devices such as scissors, dissectors, retractors, or similar instruments. To facilitate operability through the cannula, instruments adapted for laparoscopic surgery typically include a relatively narrow shaft supporting an end effector at its distal end and a handle at its proximal end. Arranging the shaft of such an instrument through the cannula allows a surgeon to manipulate the proximal handle from outside the body to cause the distal end effector to carry out a surgical procedure at a remote surgical site inside the body. This type of endoscopic procedure has proven beneficial over traditional open surgery due to reduced trauma, improved healing and other attendant advantages.

To fully realize the benefits of endoscopic surgery, instruments used for this purpose are typically designed to pass through a cannula providing a relatively small opening. For example, a cannula opening may have a diameter in the range of about five millimeters to about twelve millimeters. Even smaller openings may prove beneficial if instruments are designed without compromising the integrity or functionality of the instrument.

One type of endoscopic instrument that presents a particular challenge for designers is an electrosurgical forceps for sealing tissue. An electrosurgical forceps is a relatively complex instrument typically including several moving parts. For example, a pair of moveable jaw members may be provided for grasping tissue, and reciprocating blade may move to cut through the tissue at an appropriate time. Also contributing to the complexity is a stop member that controls the gap, or a minimum distance maintained between sealing surfaces of the jaw members. Maintaining an appropriate gap between the sealing surfaces is a necessary factor for forming an effective tissue seal. These and other manufacturing challenges become increasingly difficult to overcome when designing instruments to fit through smaller cannula openings. Conventional machining and assembly methods may lend difficulty to instrument manufacturing as the size of the components is reduced. Therefore, a jaw configuration that reduces the number or complexity of components may prove beneficial for small diameter instruments.

SUMMARY

The present disclosure describes an endoscopic bipolar forceps assembly that may be configured for use with a cannula having an opening of five millimeters or less in diameter. Several component arrangements and manufacturing process are described herein that may prove useful for larger instruments as well.

According to an aspect of the disclosure, an endoscopic forceps for joining tissue includes an elongate shaft with a distal end and a proximal end. The elongate shaft defines an instrument axis. An end effector adjacent the distal end of the elongate shaft includes first and second jaw members each supporting an opposed sealing surface for clamping tissue. At least one of the jaw members is movable relative to the instrument axis such that the jaw members are movable between a first spaced-apart configuration and a second closed configuration for grasping tissue. A cutting instrument including a reciprocating blade is translatable relative to the sealing surfaces to sever tissue clamped between the jaw members. The reciprocating blade contacts an undersurface of an opposite jaw member when the jaw members are in the second configuration to define a gap distance between the sealing surfaces. A handle adjacent to the proximal end of the elongate shaft is operable to induce motion in the jaw members to move the jaw members between the first configuration the second configuration. An actuator is operable to selectively translate the reciprocating blade.

The cutting instrument may include a distal blade and a proximal blade each contacting the undersurface of the opposite jaw member when the end effector is in the closed configuration to provide bilateral support to the opposite jaw member. The proximal blade and the distal blade may be independently movable relative to the sealing surfaces.

The reciprocating blade may include a tubular member extending proximally through the elongate shaft and a taper at a distal end of the tubular member that forms a cutting edge.

At least one of the sealing surfaces may be spring biased against a body of the respective jaw member. At least one of the first and second jaw members may include a generally flat stamped spine supporting a laterally extending backing to form the respective sealing surface. The end effector may be configured to fit through a five millimeter diameter cannula opening.

According to another aspect of the disclosure, an endoscopic forceps for joining tissue includes an elongate shaft with a distal end and a proximal end. The elongate shaft defines an instrument axis. An end effector adjacent the distal end of the elongate shaft includes first and second jaw members each supporting an opposed sealing surface for clamping tissue. At least one of the jaw members is movable relative to the instrument axis to move the jaw members a first spaced-apart configuration and a second closed configuration for grasping tissue. A cutting instrument including a reciprocating blade is translatable relative to the sealing surfaces to sever tissue clamped between the jaw members. The reciprocating blade includes a tubular member extending proximally through the elongate shaft and a taper at a distal end of the tubular member that forms a cutting edge. A handle adjacent the proximal end of the elongate shaft is operable to induce motion in the jaw members to move the jaw members between the first configuration the second configuration. An actuator is operable to selectively translate the reciprocating blade. The tubular member may include a lateral opening to provide access to an interior region of the tubular member.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
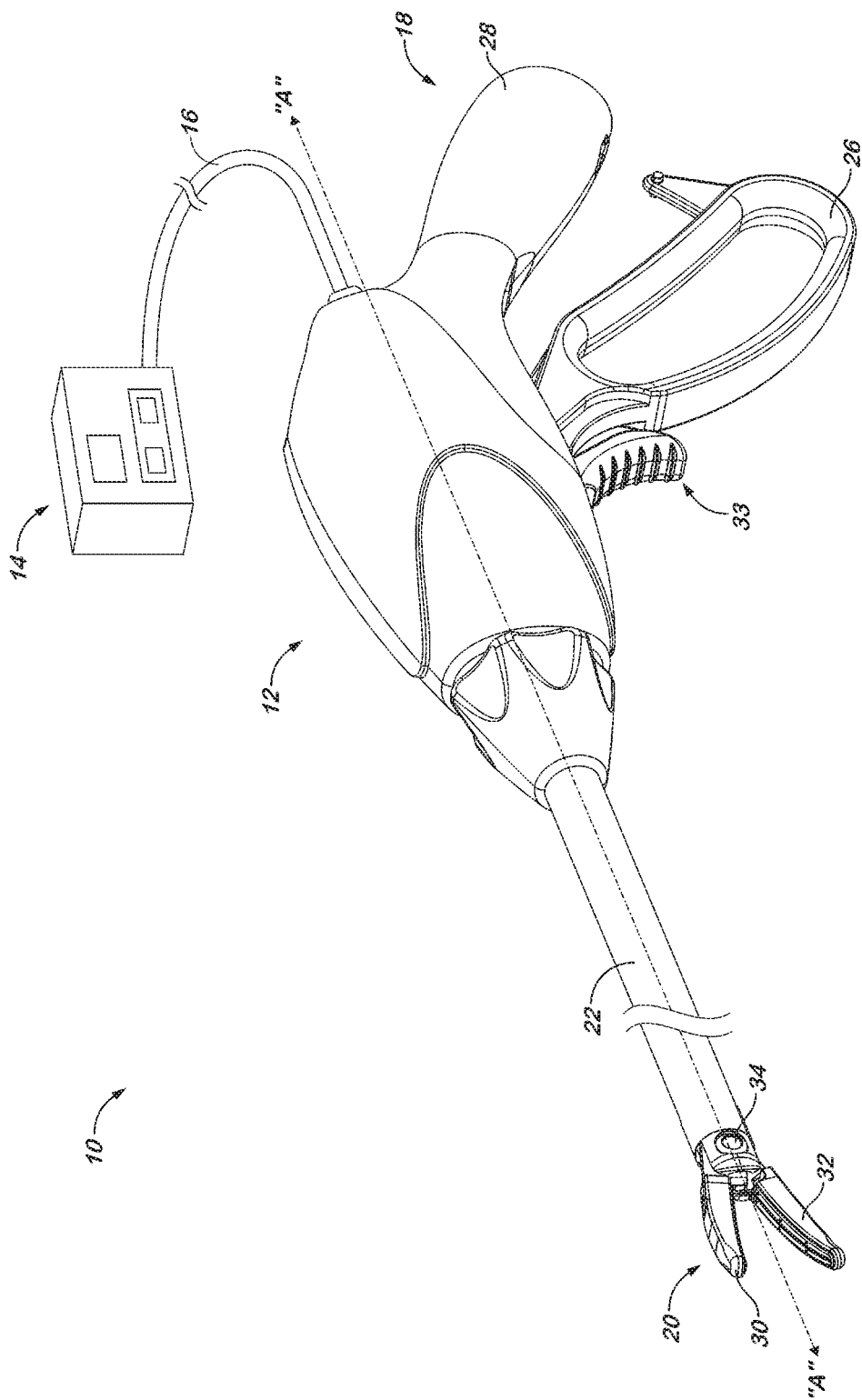
FIG. 1 is a perspective view of an electrosurgical system including an endoscopic forceps with an end effector and a generator in accordance with the present disclosure.

Detailed embodiments of the present disclosure are described herein. The disclosed embodiments are not to be interpreted as limiting, but are merely examples to provide a representative basis for the claims. In the drawings and in the description which follows, the term "proximal," as is traditional, will refer to the direction toward the operator or a relative position on the surgical device or instrument which is closer to the operator, while the term "distal" will refer to the direction away from the operator or a relative position on the instrument which is further from the operator.

Figure 5A:
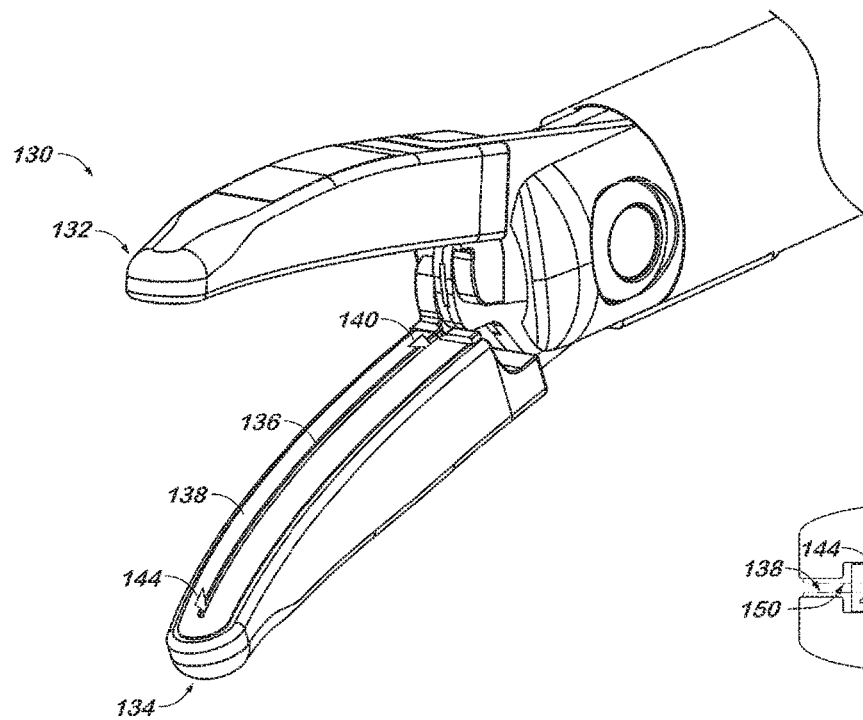
FIG. 5A is a perspective view of an alternate embodiment of an end effector in accordance with the present disclosure in an open configuration depicting a dual blade cutting instrument.

Referring initially to FIG. 1, an electrosurgical system is depicted generally as 10. The system 10 includes an endoscopic forceps 12 coupled to an electrosurgical generator 14 by a cable 16. The forceps 12 includes a handle portion 18 near a proximal end, an end effector 20 near a distal end and an elongate shaft 22 therebetween. The elongate shaft 22 defines an instrument axis "A," which may be aligned with an axis of a cannula (not shown) to insert the end effector 20 into a body cavity. Handle portion 18 is manipulatable by a surgeon from outside the body cavity to control the movement of the end effector 20 positioned inside the body cavity. For example, the surgeon may separate and approximate a pivoting handle 26 relative to a stationary handle 28 to respectively move the end effector 20 between open and closed configurations whereby a pair of jaw members 30, 32 are caused to pivot about a pivot pin 34. The motion exhibited by the jaw members 30, 32 may be described as bilateral in that both jaw members 30 and 32 move with respect to the instrument axis "A" as the end effector 20 is moved between the open and closed configurations. However, unilateral motion is also contemplated wherein an end effector (not shown) includes a stationary jaw that remains fixed relative to the instrument axis "A" and a moveable jaw that moves relative to the instrument axis "A." Handle portion 18 also supports a knife actuator 33, which is operable to selectively translate a reciprocating blade (see, e.g., FIG. 5A) through the jaw members 30, 32.

Electrosurgical generator 14 supplies the forceps 12 with electrosurgical energy, typically in the form of monopolar or bipolar radio frequency (RF) energy. In a bipolar mode, electrical energy may be provided through cable 16 and may be directed to two opposed poles on the end effector 20. The electrosurgical energy may be passed through tissue clamped between the jaw members 30, 32 to effect a tissue seal. With respect to a monopolar mode, energy of a first potential is supplied to one or both of the jaw members 30, 32 and a return pad (not shown) carries the energy back to the generator.

Figure 2:
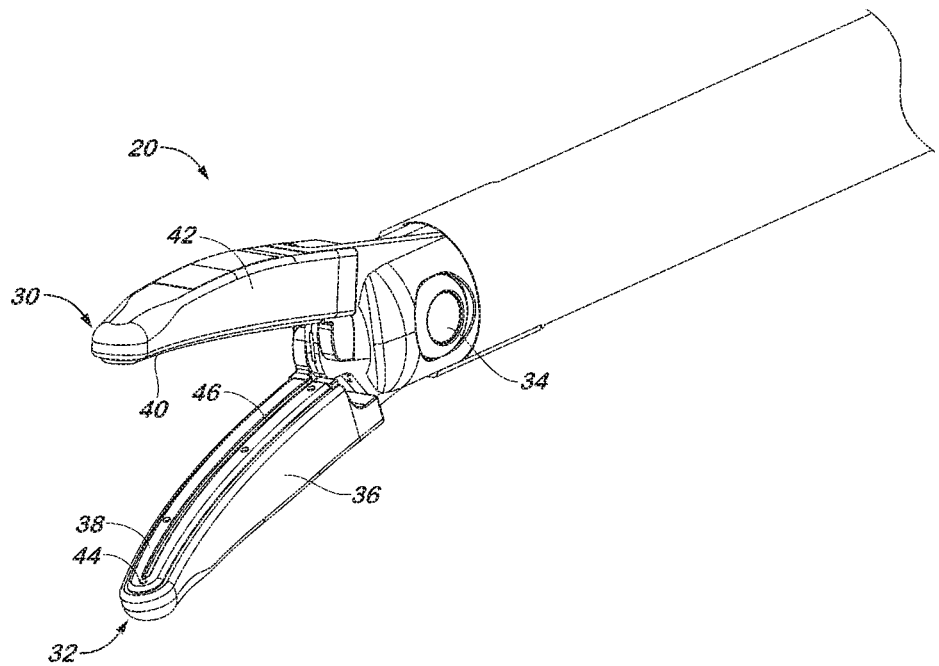
FIG. 2 is an enlarged perspective view of an end effector for use with the forceps of FIG. 1.

Referring now to FIG. 2, end effector 20 is depicted in an open configuration for receiving tissue between upper jaw member 30 and lower jaw member 32. Lower jaw member 32 includes a body 36, which provides the structural strength necessary to allow the jaw member to clamp tissue with an appropriate pressure. An appropriate sealing pressure might be, for example, in the range of from about 3 kg/cm$^2$ to about 16 kg/cm$^2$. The jaw members 30 and 32 pivot about a pivot pin 34 to move between the open and closed configurations. A sealing surface 38 is disposed on the body 36 of lower jaw member 32, and is oriented to oppose a similar sealing surface 40 on a body 42 of upper jaw member 30. The sealing surfaces 38, 40 contact the tissue when the end effector is moved to the closed configuration and deliver electrosurgical energy to the tissue. The sealing surfaces 38, 40 are generally flat to avoid current concentrations at sharp edges, and to avoid arcing between high points.

Sealing surface 38 on lower jaw member 32 is equipped with a plurality of electrically insulative stop members 44 that project from the sealing surface 38 a particular distance to control the gap between the sealing surfaces 38, 40 when end effector 20 is moved to the closed configuration. When the sealing surface 40 on the upper jaw member 30 contacts the stop members 44, sealing surface 40 is separated from sealing surface 38 by an appropriate gap for sealing tissue. An appropriate gap may be in the range of about 0.001 inches to about 0.006 inches.

A knife channel 46 extends in a generally longitudinal direction along lower jaw member 32. Knife channel 46 supports a knife blade (not shown) that may traverse the knife channel 46 to sever tissue clamped between the sealing surfaces 38, 40. For example, once a tissue seal has been effected, a surgeon may advance a knife blade distally through the knife channel 46. The knife may protrude from the knife channel 46 into a similar channel (not shown) formed in the upper jaw member 30 to ensure that any tissue captured between the jaw members 30, 32 is engaged by the knife.

Various materials and configurations may be used for constructing the jaw bodies 36, 42, the sealing surfaces 38, 40, the stop members 44 and various other components of the end effector 20. For example, jaw bodies 36, 42 may be machined from a stainless steel or similar metal, while stop members 44 may comprise a ceramic material disposed directly on the sealing surface 38. A ceramic material provides electrical insulative properties and is tolerant of the pressures and temperatures associated with tissue sealing for repeated sealing cycles. Alternatively, stop members 44 may be constructed of a plastic material molded onto the body 36 of the lower jaw member 32. Molding a plastic stop member 44 on the body 36 lower jaw member 32 may prove to be an attractive option for small instruments to permit a more significant portion of the sealing surface 38 to contact tissue. A plastic stop member 44 could be molded at a periphery of the body 36 or adjacent the knife channel 46.

Another alternative construction for jaw members 30, 32 includes forming the bodies 36, 42 from an electrically insulative material such as glass or a ceramic. The sealing surfaces 38 and 40 may be constructed with a thin coating of an electrically conductive material applied to the bodies by a physical or chemical vapor deposition process. Vapor deposition is a process commonly employed by the semiconductor industry to form thin films from electrically conductive materials such as titanium or molybdenum. A sealing surface 38, 40 constructed by vapor deposition could be electrically coupled to a source of electrosurgical energy (e.g., electrosurgical generator 14, FIG. 1) to deliver current to tissue, while the body 36, 42 could be formed into an intricate geometry to apply an appropriate pressure and form an appropriate gap. Rather than applying a sealing surface 38, 40 by vapor deposition, a glass or ceramic jaw member 30, 32 may be configured to expose a conductive wire to form sealing surfaces 38, 40.

Figure 3:
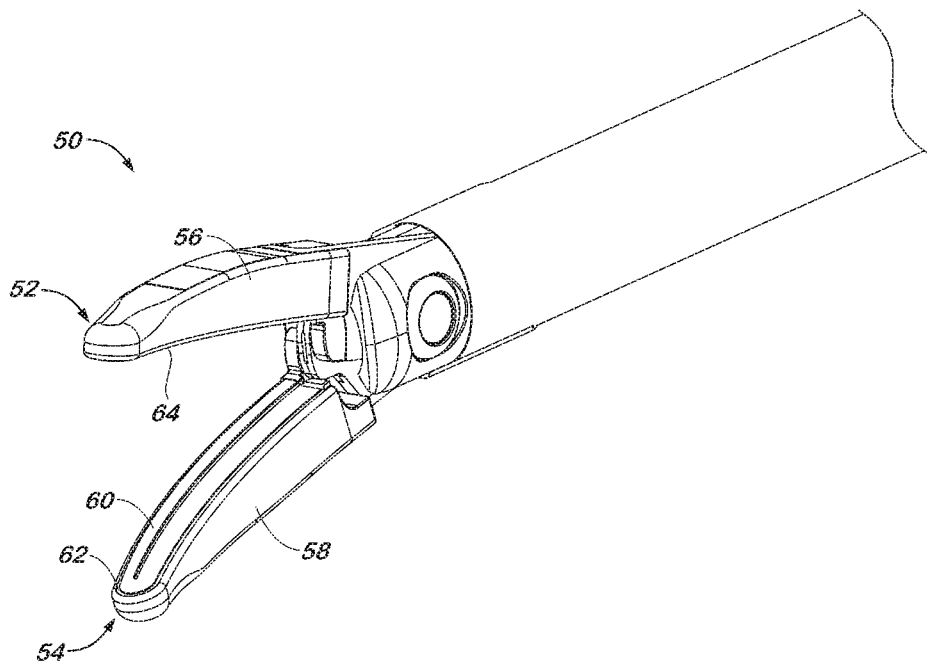
FIG. 3 is a perspective view of an alternate embodiment of an end effector in accordance with the present disclosure.

Referring now to FIG. 3, an alternate embodiment of an end effector is depicted generally as 50. End effector 50 includes an upper jaw member 52 and a lower jaw member 54. Bodies 56, 58 of the jaw members 52 and 54 are formed by a process known as metal injection molding. Metal injection molding is a process similar to thermoplastic injection molding in that complex geometries can be reproduced on a small scale. The process involves combining fine metal powders with plastic binders, which allow the metal to be injected into a mold using standard plastic injection molding machines. After the bodies 56, 58 are molded, the binders may be removed with solvents and/or thermal processes. The resultant bodies are then completed by heating or sintering at temperatures great enough to bind the powders, but not melt the metal.

Components formed by this process typically maintain tolerances of about ±0.5 percent, or down to ±0.001 inches for small dimensions, without secondary manufacturing processes. This makes metal injection molding an attractive option for producing the bodies 56, 58 of the jaw members 52 and 54, which are intended to be relatively small. Additionally, the metal substrate permits the bodies 56, 58 of the jaw members 52 and 54 to exhibit the mechanical performance properties required to effectively form a tissue seal. The metal substrate may, for example, comprise a common stainless steel such as 304L, 316L or 440C. Other alloys may be considered to enhance magnetic or thermal expansion properties of the jaw members 52, 54.

A sealing surface 60 is formed in the lower jaw member 54 such that the sealing surface 60 is recessed into the body 58. A periphery 62 of the body 58 extends around the sealing surface 60 to define a gap, or the minimum distance that may be maintained between sealing surface 60 and a sealing surface 64 disposed on the upper jaw member. The periphery 62 may include a semi-conductive film to provide insulation. Sealing surface 64 may be recessed into the body 56 of the upper jaw, or the sealing surface 64 may lie flush with an exterior surface of the upper jaw member 52. The recess may be roughly formed in the body 58 with the metal injection molding process described above. Fine surface adjustments may be made to the flatness or surface finish of the sealing surface 64 by a machining process such as wire EDM manufacturing.

Wire EDM, or electrical discharge machining, is a high precision manufacturing process capable of forming a sealing surface 64 suitably flat and smooth to permit an effective tissue seal. Tolerances of ±0.0002 inches are routinely achieved by the wire EDM process. The process involves removing metal from the jaw body 58 by generating a series of electrical arcs between the body 58 and a moveable electrode in the presence of an electric field. The electrical arcs remove metal along the cutting path by melting and vaporization.

Referring now to FIGS. 4A through 4D, several configurations are discussed for a small jaw member. Conventional machining and assembly methods may lend difficulty to instrument manufacturing as the size of the components is reduced. Therefore, a jaw configuration that reduces the number or complexity of components may prove beneficial for small diameter instruments.

Figure 4A:
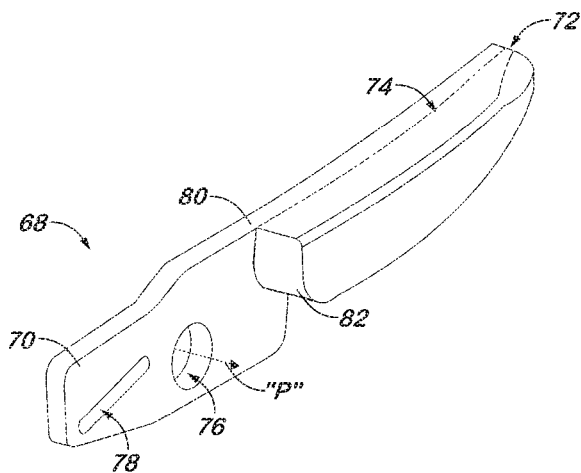
FIGS. 4A through 4C are perspectives views of alternate embodiments of jaw members designed to facilitate manufacturing and assembly of the forceps of FIG. 1 in accordance the present disclosure.

Jaw member 68, depicted in FIG. 4A, includes a proximal projection 70 extending from a distal region 72. The distal region 72 may support a sealing surface 74 thereon, while the proximal projection 70 includes a bore 76 and an angled slot 78, which work in combination to cause the jaw member 68 to move. The bore 76 defines a pivot axis "P" about which the jaw member 68 may pivot, and is configured to receive a pivot pin or boss (not shown) therethrough. The angled slot 78 is configured to receive a longitudinally moveable cam member (not shown) to drive the pivotal motion of jaw member 68 about the pivot axis "P." Since the proximal projection 70 drives the motion of the jaw member 68, a certain degree of rigidity of the proximal projection 70 may be beneficial. The rigidity may be supplied by a stamped spine 80.

Stamped spine 80 is a generally flat component formed by stamping a particular profile from a sheet metal or other rigid flat stock material. The spine 80 may be stamped to define the external shape of the proximal projection 70, and may extend the full length of the jaw member 68 into the distal region 72. Stamping is a common process in metal working, wherein a press and a die apply shear pressure to a stock material to form a particular shape. High tolerances may be achieved by stamping, and thus the need for a secondary machining process may be avoided. For example, the spine 80 may be formed including the bore 76 and the slot 78 in a single stamping operation.

The stamped spine 80 supports a backing 82 thereon. The backing 82 extends laterally from the stamped spine 80 to define a width of a sealing surface 74. The backing 82 may extend in a single direction as shown, or in various lateral and vertical directions to form other surfaces of the jaw member 68. Backing 82 may comprise a plastic material molded, or otherwise affixed to the spine 80. An appropriate plastic backing may be configured to project from the jaw member 68 to control a gap between sealing surface 74 and an opposed sealing surface (not shown). Backing 82 may alternatively be constructed from a metallic material such as zinc, magnesium or aluminum.

Figure 4B:
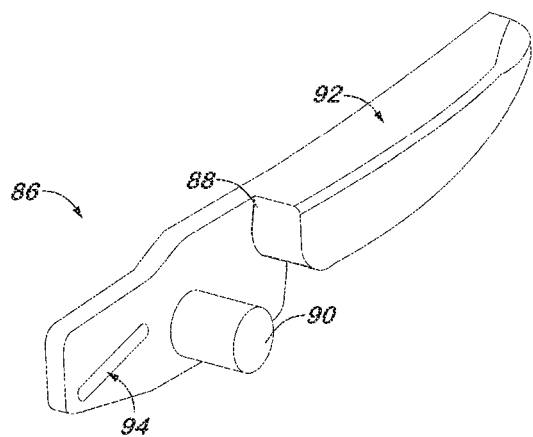

Jaw member 86, depicted in FIG. 4B, may also be formed by a process of minimal complexity. Jaw member 86 includes a body 88 and a pivot pin 90. The body 88 supports a sealing surface 92, and includes a slot 94 to drive a pivotal motion of jaw member 86 about the pivot pin 90. The body 88 may be formed as a die cast component from a material such as zinc, aluminum or magnesium. Die casting involves inserting molten metal under pressure into a die cavity and allowing the metal to solidify. Die casting is most commonly used with non-ferrous metals such as those mentioned above. It may be beneficial, though, to construct pivot pin 90 from a ferrous steel insert, which may be press fit, insert-molded in the die casting, or otherwise joined to the non-ferrous body 88.

Figure 4C:
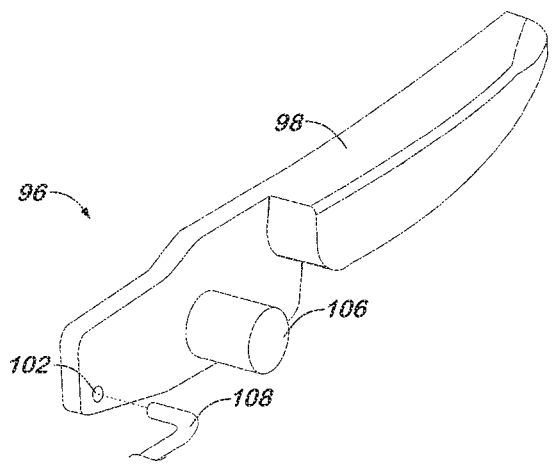

Jaw member 96, depicted in FIG. 4C, includes a sealing surface 98 and an actuation bore 102. Actuation bore 102 is offset from a pivot pin 106 such that the actuation bore 102 may be engaged by conductive pull wire 108 to cause the jaw member 96 to pivot. Pull wire 108 may be mechanically coupled an actuation mechanism such as pivoting handle 26 (FIG. 1) to move the pull wire 108 longitudinally with respect to the pivot pin 106 and thus pivot the jaw member. Pull wire 108 may also be electrically coupled to a source of electrosurgical energy to deliver power to the sealing surface 98. Since separate mechanical and electrical actuation mechanisms may not be necessary, the number of parts required may be reduced by permitting the pull wire 108 to perform both electrical and mechanical functions.

Figure 4D:
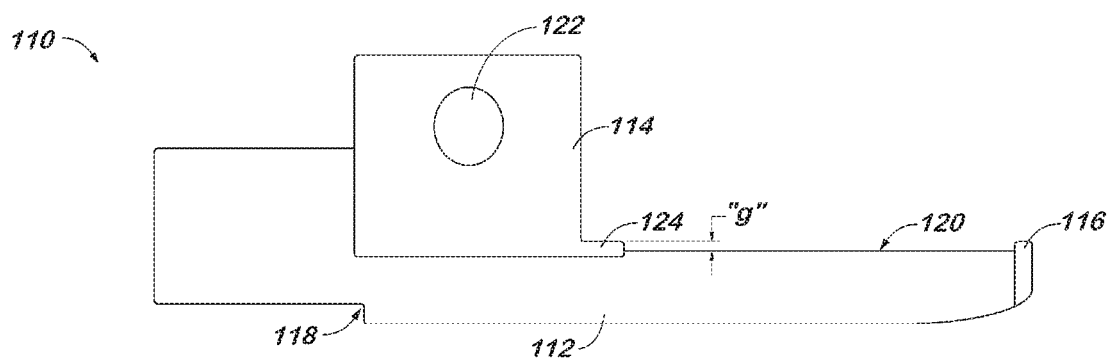
FIG. 4D is a side, elevational view of another alternate embodiment of a jaw member in accordance with the present disclosure wherein appendages define a gap for maintaining the jaw members a fixed distance relative to one another for sealing tissue.

Jaw member 110, depicted in FIG. 4D includes a body 112 and appendages 114 and 116. The body 112 may be constructed of a stamped metallic plate as discussed above, or may alternatively be constructed of a metalized carbon, plastic or similar material. A metalized material generally is impregnated with a metal to impart metallic properties to the material. For example, a metalized body 112 may be capable of conducting an electrosurgical current from a solder joint 118 at a proximal region of the jaw member 110 where the jaw member may be coupled to an elongate shaft 18 (FIG. 1) to a sealing surface 120. The underlying substrate of the metalized material may be selected for other characteristics such as thermal expansion, manufacturability or a readiness to adhere to appendages 114 and 116.

The appendages 114 and 116 may be constructed of a ceramic to provide electrical insulation to the jaw member 110. For example, proximal appendage 114 includes a pivot bore 122 for receiving a pin (not shown), which may be electrically isolated from the body 112 due to the ceramic construction of the proximal appendage 114. Proximal appendage 114 also provides a step 124 to define a gap distance "g" from sealing surface 120. Distal appendage 116 may also protrude above the sealing surface 120 by the gap distance "g" to provide bilateral support for an opposing jaw member (not shown).

Referring now to FIGS. 5A through 5D, several embodiments are discussed relating to small jaw configurations that employ components for cutting tissue. End effector 130 depicted in FIG. 5A includes an upper jaw member 132 movably disposed with respect to a lower jaw member 134.

The lower jaw member 134 includes a knife channel 136 extending in a generally longitudinal direction through a u-shaped sealing surface 138. A cutting instrument includes a proximal blade 140 and a distal blade 144 projecting from the knife channel 136 to permit the end effector 130 to selectively cut tissue.

The proximal blade 140 may translate to traverse the knife channel 136 in a distal direction to cut tissue clamped between the upper and lower jaw members 132 and 134, while the distal blade 144 may traverse the channel 136 in a proximal direction to cut tissue. The two blades 140, 144 may be selectively and independently actuated from a handle 18 (FIG. 1) such that one blade remains stationary within the knife channel 136 while the other cuts tissue, or alternatively both blades may be configured to move together. Also, the two blades 140, 144 may be laterally aligned within the channel 136 such that the two blades 140, 144 contact one another when fully approximated, or alternatively the two blades 140, 144 may be laterally offset such that the blades may move longitudinally past one another as they traverse the channel 136.

Figure 5B:
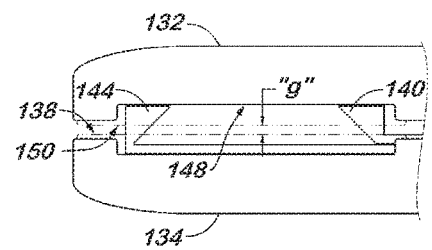
FIG. 5B is a schematic view of the end effector of FIG. 5A in a closed configuration.

As depicted in FIG. 5B, when the upper and lower jaw members are moved to a closed configuration, an undersurface 148 of the upper jaw member 132 contacts the blade members 140, 144. Thus, the two blade members 140, 144 define the gap distance "g" between the sealing surface 138 of the lower jaw member 134 and an opposed sealing surface 150 of the upper jaw member 132 shown in phantom. This configuration may eliminate the need for stop members positioned on surfaces which might otherwise be used for sealing tissue, such as the stop members 44 described in reference to FIG. 2.

Figure 5C:
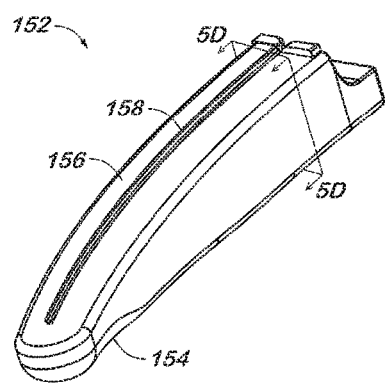
FIG. 5C is a perspective view of an alternate embodiment of a jaw member in accordance with the present disclosure depicting a knife channel wall projecting above a seal plate to define a gap distance for sealing tissue.
Figure 5D:
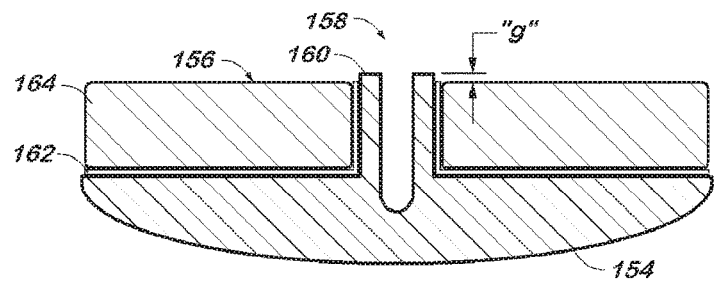
FIG. 5D is an enlarged, cross-sectional view of the jaw member of FIG. 5C taken along the plane 5D-5D.

Jaw member 152 depicted in FIGS. 5C and 5D includes an alternate configuration for a maintaining a specified distance between sealing surfaces. Jaw member 152 includes a body 154 supporting a sealing surface 156 thereon. A knife channel 158 extends through the jaw member 152 and includes an elevated surface with respect to the sealing surface 156.

The body 154 of the jaw may be a die cast or metal injection molded component having the knife channel 158 formed integrally therein. A channel wall 160 protrudes from a laterally interior region of the body 154 to define the knife channel 158. Laterally outward from the channel wall 160, a layer of insulation 162 electrically separates the body 154 from a seal plate 164. The channel wall 160 extends beyond the sealing surface 156 of the seal plate 160 by a distance "g" such that a gap may be formed between the sealing surface 156 and a sealing surface of an opposed jaw member (not shown).

Figure 5E:
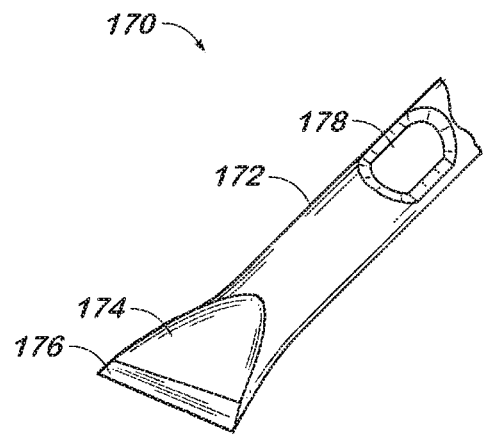
FIG. 5E is a partial perspective view of a cutting instrument in accordance with the present disclosure.

Referring now to FIG. 5E, a cutting instrument such as knife 170 may be advanced through a channel to cut tissue. Knife 170 includes a tubular member 172. The tubular member 172 is crimped such that a taper 174 is formed closing a distal end of the tubular member 172. The closed distal end may be sharpened to form a cutting edge 176. The tubular body provides an interior region through which electrical conductors, fluid conduits or other elongate components may be disposed. An opening such as lateral opening 178 may be formed in the tubular member 172 to provide access to the interior region. The tubular member 172 may extend proximally through an elongate shaft 22 (FIG. 1) such that knife 170 may be controlled from a proximal end of an instrument.

Figure 5F:
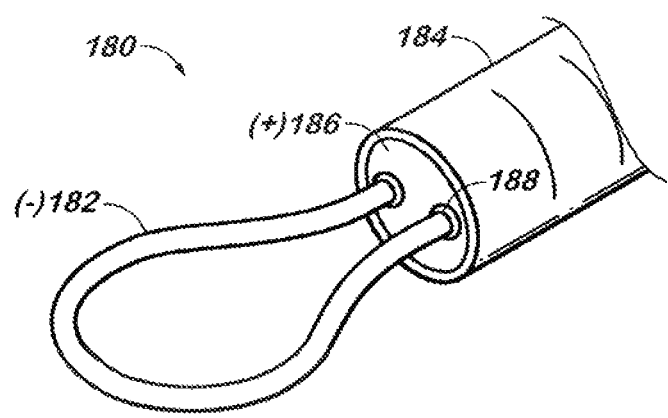
FIG. 5F is a partial perspective view of an alternate embodiment of a cutting instrument in accordance with the present disclosure having a wire loop for capturing tissue

Referring now to FIG. 5F, a snare 180 is depicted, which may be incorporated into a small instrument to permit tissue to be cut. The snare 180 includes a wire loop 182 extending from a distal end of a sheath 184. The wire loop 182 may be coupled to an actuation mechanism (not shown) at a proximal end of the instrument permitting the wire loop 182 to be extended from and withdrawn into the distal end of the sheath 184. The wire loop 182 may be coupled to a source of electrosurgical energy such that wire loop 182 exhibits a first electrical polarity (−). A forward surface 186 of the sheath 184 may exhibit a second electrical polarity (+) separated from the wire loop by insulating grommets 188.

Tissue may be captured within the wire loop 182. As the wire loop 182 is withdrawn into the sheath 184, the tissue may be drawn toward the forward surface 186. An electrical current may be transmitted through the tissue between the wire loop 182 and the forward surface 186 such that the tissue may be electrosurgically cut.

Snare 180 represents a relatively simple mechanism, which may be readily incorporated into a small diameter endoscopic instrument, or may be configured for use in open surgical procedures. Other embodiments include a monopolar snare 180 wherein wire loop 182 and/or the forward surface 186 exhibits a first electrical polarity (−) and a return pad (not shown) exhibits the second electrical polarity (+), and a rigid snare 180 having a wire loop 182 that does not withdraw into the sheath 184.

Figure 5G:
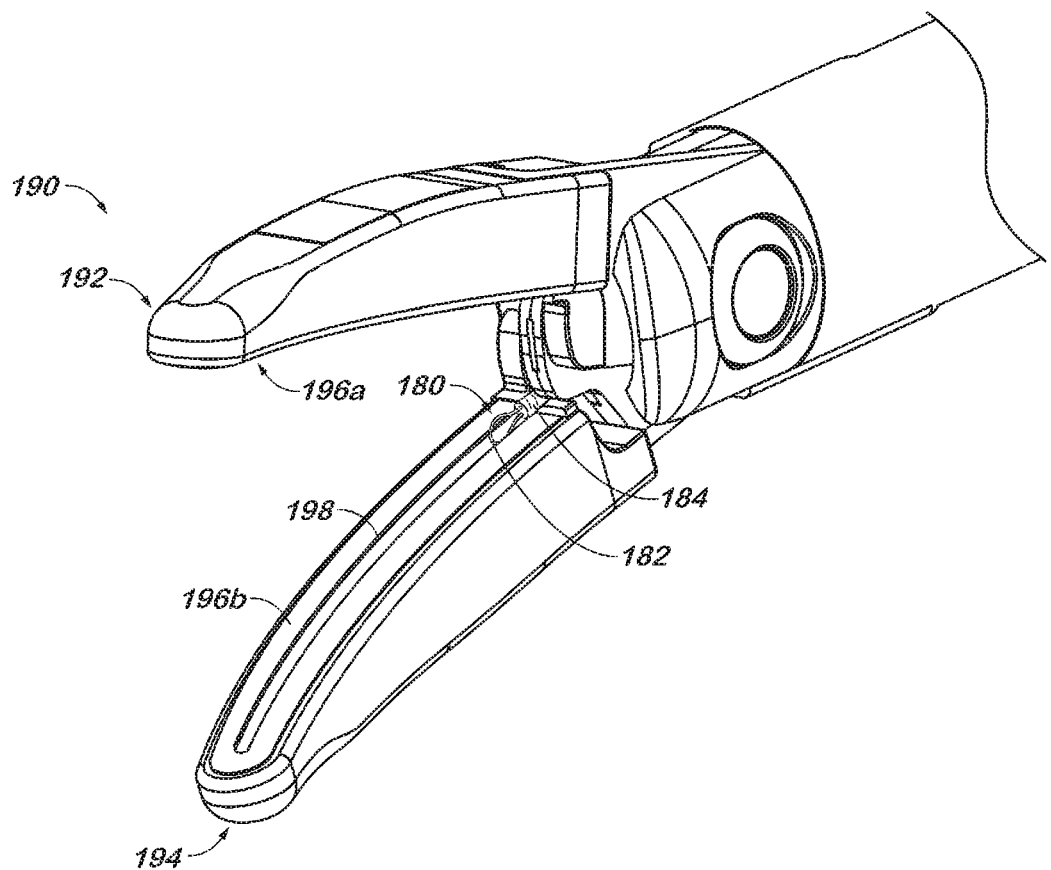
FIG. 5G is a perspective view of an alternate embodiment of an end effector in accordance with the present disclosure in an open configuration depicting a wire loop cutting instrument.

Referring now to FIG. 5G, end effector 190 includes an upper jaw member 192 movably coupled to a lower jaw member 194. The upper and lower jaw members 194 include respective opposed sealing surfaces 196a, 196b thereon for contacting tissue. A channel 198 extends in a generally longitudinal direction through the sealing surface 196b on the lower jaw member 194, and provides a path through which snare 180 may be advanced. The sheath 184 of snare 180 may be operatively coupled to an actuator (not shown) such that the snare 180 may reciprocate in the channel 198. Thus, the wire loop 182 may be advanced to a distal end of the channel 198 and withdrawn to the proximal end of the channel 198.

The wire loop 182 may exhibit a first electrical polarity (−) while the sealing surfaces 196a, 196b exhibit a second electrical polarity (+) to permit an electrical current to be transmitted through tissue captured between the jaw members 192, 194. Alternatively, the sealing surfaces 196a (−), 196b (+) may exhibit opposite electrical polarities, while wire loop 182 (+) exhibits one or the other polarity. The snare 180 may thus serve as a reciprocating blade for electrosurgically cutting tissue as the snare 180 reciprocates within the channel 198. The snare 180 may be configured in any manner described above with reference to FIG. 5F. For example, the snare 180 may be retractable such that the wire loop 182 may be withdrawn into the sheath or rigid such that the wire loop 182 does not retract into the sheath 184.

Figure 6:
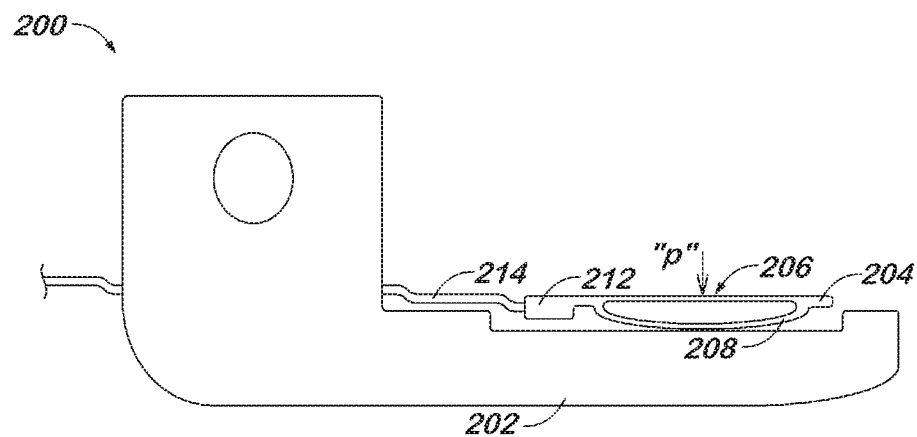
FIG. 6 is a schematic view of an alternate embodiment of a jaw member in accordance with the present disclosure wherein a spring loaded seal plate is movable relative to the jaw member to influence a sealing pressure applied to tissue.

Referring now to FIG. 6, a jaw member 200 is depicted, which is configured to clamp tissue with an appropriate pressure to effectuate tissue sealing. Jaw member 200 generally includes a body 202 and a spring loaded seal plate 204. The seal plate 204 provides a generally flat sealing surface 206 on an upper portion thereof and includes a resilient lower portion 208. The resilient lower portion 208 of the seal plate 204 may be elastically deformed against the body 202 when a pressure is applied to the seal plate 204 in the direction of arrow "p." Thus, the sealing surface 206b is movable relative to the body 202 in a direction generally perpendicular to the sealing surface 206. The seal plate 204 may be constructed from spring steel, nitinol or other alloy that permits the seal plate 204 to flex.

A connector portion 212 of the seal plate receives an electrical lead 214 in a manner similar to a standard wire terminal connector. The electrical lead 214 may be crimped, soldered or otherwise placed in electrical communication with the connector portion 212. In this way, an electrosurgical current may be transmitted between the lead 214 and the sealing surface 206.

Although the foregoing disclosure has been described in some detail by way of illustration and example, for purposes of clarity or understanding, it will be obvious that certain changes and modifications may be practiced within the scope of the appended claims.

What is claimed:

1. A forceps, comprising:
an elongated shaft including a distal end and a proximal end, the elongated shaft defining an instrument axis;
an end effector adjacent the distal end of the elongate shaft, the end effector including first and second jaw members each supporting a corresponding sealing surface thereon for clamping tissue therebetween, wherein at least one of the first and second jaw members is movable relative to the instrument axis to move the jaw members between a first spaced-apart configuration and a second closed configuration for grasping tissue;
a cutting instrument including a reciprocating blade translatable relative to the sealing surfaces to sever tissue clamped between the jaw members, wherein the reciprocating blade includes a wire loop adaptable to couple to a source of electrosurgical energy;
a handle adjacent the proximal end of the elongated shaft, the handle operable to induce motion in the jaw members to move the jaw members between the first configuration and second configuration;
an actuator operable to selectively translate the reciprocating blade; and
a sheath having a distal surface, wherein the wire loop is configured to extend from the distal surface of the sheath, the wire loop having a first electrical polarity and the distal surface of the sheath having a second electrical polarity, and wherein the wire loop is configured to pass through an insulating grommet secured to the distal surface of the sheath to electrically isolate the wire loop from the distal surface.

2. The forceps according to claim 1, wherein the wire loop exhibits a first electrical polarity, and wherein at least one of the sealing surfaces supported by the jaw members exhibits a second electrical polarity.

3. The forceps according to claim 2, wherein the second electrical polarity is opposite the first electrical polarity.

4. The forceps according to claim 1, wherein the wire loop has an extended position in which the wire loop extends from the distal surface of the sheath and a withdrawn position in which the wire loop is withdrawn into the sheath.

5. The forceps according to claim 1, wherein the wire loop is rigid.

* * * * *